US008989849B2

(12) United States Patent
Milner et al.

(10) Patent No.: US 8,989,849 B2
(45) Date of Patent: *Mar. 24, 2015

(54) ROTATING OPTICAL CATHETER TIP FOR OPTICAL COHERENCE TOMOGRAPHY

(75) Inventors: Thomas E. Milner, Austin, TX (US); Marc D. Feldman, Austin, TX (US); Jung-Hwan Oh, Austin, TX (US); Shaochen Chen, Austin, TX (US); Paul Castella, Austin, TX (US)

(73) Assignee: Board of Regents, the University of Texas System, Austin, TX (US)

(*) Notice: Subject to any disclaimer, the term of this patent is extended or adjusted under 35 U.S.C. 154(b) by 361 days.

This patent is subject to a terminal disclaimer.

(21) Appl. No.: 12/911,541

(22) Filed: Oct. 25, 2010

(65) Prior Publication Data
US 2011/0152771 A1 Jun. 23, 2011

Related U.S. Application Data

(63) Continuation of application No. 11/551,684, filed on Oct. 20, 2006, now Pat. No. 7,853,316, and a
(Continued)

(51) Int. Cl.
*A61B 8/00* (2006.01)
*A61B 1/06* (2006.01)
(Continued)

(52) U.S. Cl.
CPC ............ *A61B 5/6852* (2013.01); *A61B 8/4461* (2013.01); *A61B 6/12* (2013.01);
(Continued)

(58) Field of Classification Search
CPC .. A61B 5/0084; A61B 5/0066; A61B 5/6852; A61B 8/4461; A61B 8/12; A61B 1/3137; A61B 1/00183; A61N 2007/0091
USPC .......................................... 600/466, 467, 473
See application file for complete search history.

(56) References Cited

U.S. PATENT DOCUMENTS

| 1,467,672 A | 9/1923 | Kaplan | 415/129 |
| 2,334,302 A | 11/1943 | Akins | 415/75 |

(Continued)

FOREIGN PATENT DOCUMENTS

| DE | 29521096 | 8/1996 | A61B 17/22 |
| EP | 147192 | 7/1985 | A61B 17/22 |

(Continued)

OTHER PUBLICATIONS

Davies, M.J., et al., "Plaque Fissuring—The Cause of Acute Myocardial Infarction, Sudden Ischaemic Death, and Crescendo Agina", *British Heart Journal*, vol. 53, pp. 363-373, (1985).
(Continued)

*Primary Examiner* — Long V Le
*Assistant Examiner* — Helene Bor
(74) *Attorney, Agent, or Firm* — David G. Rosenbaum; J. Peter Paredes; Rosenbaum IP, P.C.

(57) ABSTRACT

The present invention relates to a rotating catheter tip for optical coherence tomography based on the use of an optical fiber that does not rotate, that is enclosed in a catheter, which has a tip rotates under the influence of a fluid drive system to redirect light from the fiber to a surrounding vessel and the light reflected or backscattered from the vessel back to the optical fiber.

20 Claims, 5 Drawing Sheets

Related U.S. Application Data continuation-in-part of application No. 10/548,982, filed as application No. PCT/US2004/012773 on Apr. 23, 2004, now Pat. No. 7,711,413.

(60) Provisional application No. 60/728,481, filed on Oct. 20, 2005, provisional application No. 60/466,215, filed on Apr. 28, 2003.

(51) Int. Cl.

| | |
|---|---|
| *A61B 5/00* | (2006.01) |
| *A61B 6/12* | (2006.01) |
| *A61B 1/00* | (2006.01) |
| *A61N 7/00* | (2006.01) |
| *A61B 1/313* | (2006.01) |

(52) U.S. Cl.
CPC .......... *A61B 5/0084* (2013.01); *A61B 1/00183* (2013.01); *A61B 5/0066* (2013.01); *A61N 2007/0091* (2013.01); *A61B 1/3137* (2013.01)
USPC ............ 600/478; 600/466; 600/473; 600/182

(56) References Cited

U.S. PATENT DOCUMENTS

| | | | | |
|---|---|---|---|---|
| 3,945,375 | A | 3/1976 | Banko | 600/104 |
| 4,631,052 | A * | 12/1986 | Kensey | 604/22 |
| 4,648,892 | A | 3/1987 | Kittrell et al. | 65/387 |
| 5,176,141 | A | 1/1993 | Bom et al. | 600/467 |
| 5,240,003 | A | 8/1993 | Lancee et al. | 600/467 |
| 5,271,402 | A | 12/1993 | Yeung et al. | 600/437 |
| 5,438,997 | A | 8/1995 | Sieben et al. | 128/662.06 |
| 5,507,294 | A | 4/1996 | Lum et al. | 600/459 |
| 5,635,784 | A | 6/1997 | Seale | 310/90.5 |
| 5,920,390 | A | 7/1999 | Farahi et al. | 356/345 |
| 5,957,941 | A | 9/1999 | Ream | 606/159 |
| 6,001,112 | A | 12/1999 | Taylor | 606/159 |
| 6,069,698 | A | 5/2000 | Ozawa et al. | 356/345 |
| 6,134,003 | A | 10/2000 | Tearney et al. | 356/479 |
| 6,134,033 | A | 10/2000 | Bergano et al. | 359/122 |
| 6,264,608 | B1 | 7/2001 | Schatzle et al. | 600/439 |
| 6,357,998 | B1 | 3/2002 | Rosefsky | 415/66 |
| 2002/0198457 | A1 | 12/2002 | Tearney et al. | 600/476 |

FOREIGN PATENT DOCUMENTS

| | | | | |
|---|---|---|---|---|
| JP | 08-238239 | 9/1996 | ............... | A61B 8/00 |
| JP | 2000-070270 | 3/2000 | ............... | A61B 8/12 |
| JP | 2000-507860 | 6/2000 | ............... | A61F 7/00 |
| WO | WO 2004-096049 | 11/2004 | ............... | A61B 6/00 |

OTHER PUBLICATIONS

Davies, M.J., et al., "Risk of Thrombosis in Human Atherosclerotic Plaques: Role of Extracellular Lipid, Macrophage, and Smooth Muscle Cell Content", *British Heart Journal*, vol. 69, pp. 377-381, (1993).

Driggers, R.G. (ed) *Encyclopedia of Optical Engineering*, New York, Marcel Dekker, vol. 2, pp. 1594, (2003).

Feldchtein, F.I., et al., "Endoscopic Applications of Optical Coherence Tomography", *Optics Express*, vol. 3, No. 6, pp. 257-270, (Sep. 14, 1998).

Feldchtein, V.M, et al., "Design and Performance of an Endoscopic OCT System for In Vivo Studies of Human Mucosa", *Technical Digest for Summaries of Papers—Conference on Lasers and Electro-Optics Conference Edition, Technical Digest Series*, vol. 6., pp. 122-123, (1998).

Jang, I.K., et al., "Visualization of Cornoary Atheerosclerotic Plaques in Patients Using Optical Coherence Tomography: Comparison With Intravascular Ultrasound", *Journal of the American College of Cardiology*, vol. 29, No. 4, pp. 604-609, (2002).

Jesser, C.A., et al., "High Resolution Imaging of Transitional Cell Carcinoma with Optical Coherence Tomography: Feasibility for the Evaluation of Bladder Pathology", *The British Journal of Radiology*, vol. 72, pp. 1170-1176, (1999).

Little, W.C., et al., "The Underlying Coronary Lesion in Myocardial Infarction: Implications for Coronary Angiography", *Clinical Cardiology*, vol. 14, No. 11, pp. 868-874, (Nov. 1991).

Nisssen, S., "Coronary Angiography and Intravascular Ultrasound", *American Journal of Cardiology*, vol. 87 (suppl), pp. 15A-20A, (2001).

Rabbani, R., et al., "Strategies to Achieve Coronary Arterial Plaque Stabilization", *Cardiovascular Research*, vol. 41, pp. 402-417, (1999).

Supplementary Partial European Search Report for published European application EP 1620013, pp. 1-4, (Apr. 15, 2009).

Supplementary Partial European Search Report for published European application EP 1948021, pp. 1-6, (Oct. 30, 2009).

Tearney, G.J., et al., "Endoscopic optical coherence tomography", *Proceedings of SPIE—International Society for Optical Engineering*, vol. 2979, pp. 2-5, (1997).

Villard, J.W., et al., "Use of a Blood Substitute to Determine Instantaneous Murine Right Ventricular Thickening With Optical Coherence Tomography", *Circulation, Journal of the American Heart Association*, vol. 105, pp. 1843-1849, (2002).

* cited by examiner

ROTATING OPTICAL CATHETER TIP FOR OPTICAL COHERENCE TOMOGRAPHY

CROSS-REFERENCE TO RELATED APPLICATIONS

The present application is a continuation from U.S. patent application Ser. No. 11/551,684 filed Oct. 20, 2006, (now U.S. Pat. No. 7,853,316), which claims priority to U.S. Provisional Patent Application Ser. No. 60/728,481, filed Oct. 20, 2005, and U.S. patent application Ser. No. 11/551,684 is a continuation-in-part "CIP" of U.S. patent application Ser. No. 10/548,982, which was filed Sept. 7, 2005 and granted a U.S. national stage filing date of May 2, 2006 (now U.S. Pat. No. 7,711,413), which claims priority to PCT International Patent Application No. PCT/US2004/012773, filed Apr. 23, 2004 and which claims priority to U.S. Provisional Patent Application Ser. No. 60/466,215, filed Apr. 28, 2003, all of which are hereby expressly incorporated by reference.

BACKGROUND OF THE INVENTION

The present invention relates to catheter probes based on the use of a fiber that does not rotate. More specifically, the present invention relates to optical coherence tomography based on the use of an optical fiber that does not rotate, which is enclosed in a catheter portion.

Myocardial infarction or heart attack remains the leading cause of death in our society. Unfortunately, most of us can identify a family member or close friend that has suffered from a myocardial infarction. Until recently many investigators believed that coronary arteries critically blocked with atherosclerotic plaque that subsequently progressed to total occlusion was the primary mechanism for myocardial infarction. Recent evidence from many investigational studies, however, clearly indicates that most infarctions are due to sudden rupture of non-critically stenosed coronary arteries due to sudden plaque rupture. For example, Little et al. (Little, W C, Downes, T R, Applegate, R J. The underlying coronary lesion in myocardial infarction: implications for coronary angiography. Clin Cardiol 1991, 14: 868-874, incorporated by reference herein) observed that approximately 70% of patients suffering from an acute plaque rupture were initiated on plaques that were less than 50% occluded as revealed by previous coronary angiography. This and similar observations have been confirmed by other investigators (Nissen, S. Coronary angiography and intravascular ultrasound. Am J Cardiol 2001, 87 (suppl): 15A-20 A, incorporated by reference herein).

The development of technologies to identify these unstable plaques holds the potential to decrease substantially the incidence of acute coronary syndromes that often lead to premature death. Unfortunately, no methods are currently available to the cardiologist that may be applied to specify which coronary plaques are vulnerable and thus prone to rupture. Although treadmill testing has been used for decades to identify patients at greater cardiovascular risk, this approach does not have the specificity to differentiate between stable and vulnerable plaques that are prone to rupture and frequently result in myocardial infarction. Inasmuch as a great deal of information exists regarding the pathology of unstable plaques (determined at autopsy) technologies based upon identifying the well described pathologic appearance of the vulnerable plaque offers a promising long term strategy to solve this problem.

The unstable plaque was first identified and characterized by pathologists in the early 1980's. Davis and coworkers noted that with the reconstruction of serial histological sections in patients with acute myocardial infarctions associated with death, a rupture or fissuring of athermanous plaque was evident (Davis M J, Thomas A C. Plaque fissuring: the cause of acute myocardial infarction, sudden death, and crescendo angina. Br Heart J 1985; 53: 3 63-37 3, incorporated by reference herein). Ulcerated plaques were further characterized as having a thin fibrous cap, increased macrophages with decreased smooth muscle cells and an increased lipid core when compared to non-ulcerated atherosclerotic plaques in human aortas (Davis M J, Richardson E D, Woolf N. Katz O R, Mann J. Risk of thrombosis in human atherosclerotic plaques: role of extracellular lipid, macrophage, and smooth muscle cell content, incorporated by reference herein). Furthermore, no correlation in size of lipid pool and percent stenosis was observed when imaging by coronary angiography. In fact, most cardiologists agree that unstable plaques progress to more stenotic yet stable plaques through progression via rupture with the formation of a mural thrombus and plaque remodeling, but without complete luminal occlusion (Topol E J, Rabbaic R. Strategies to achieve coronary arterial plaque stabilization. Cardiovasc Res 1999; 41: 402-417, incorporated by reference herein). Neovascularization with intra-plaque hemorrhage may also play a role in this progression from small lesions, i.e., those less than about 50% occluded, to larger significant plaques. Yet, if the unique features of unstable plaque could be recognized by the cardiologist and then stabilized, a dramatic decrease may be realized in both acute myocardial infarction and unstable angina syndromes, and in the sudden progression of coronary artery disease.

SUMMARY OF THE INVENTION

The present invention uses depth-resolved light reflection or Optical Coherence Tomography (OCT) to identify the pathological features that have been identified in the vulnerable plaque. In OCT, light from a broad band light source or tunable laser source is split by an optical fiber splitter with one fiber directing light to the vessel wall and the other fiber directing light to a moving reference minor. The distal end of the optical fiber is interfaced with a catheter for interrogation of the coronary artery during a heart catheterization procedure. The reflected light from the plaque is recombined with the signal from the reference minor forming interference fringes (measured by an photovoltaic detector) allowing precise depth-resolved imaging of the plaque on a micron scale.

OCT uses a superluminescent diode source or tunable laser source emitting a 1300 nm wave length, with a 50-250 nm band width (distribution of wave length) to make in situ tomographic images with axial resolution of 2-20 μm and tissue penetration of 2-3 mm. OCT has the potential to image tissues at the level of a single cell. In fact, the inventors have recently utilized broader band width optical sources so that axial resolution is improved to 4 um or less. With such resolution, OCT can be applied to visualize intimal caps, their thickness, and details of structure including fissures, the size and extent of the underlying lipid pool and the presence of inflammatory cells. Moreover, near infrared light sources used in OCT instrumentation can penetrate into heavily calcified tissue regions characteristic of advanced coronary artery disease. With cellular resolution, application of OCT may be used to identify other details of the vulnerable plaque such as infiltration of monocytes and macrophages. In short, application of OCT can provide detailed images of a pathologic specimen without cutting or disturbing the tissue.

One concern regarding application of this technology to image atherosclerotic plaques within the arterial lumen is the strong scattering of light due to the presence of red blood cells. Once a catheter system is positioned in a coronary artery, the blood flow between the OCT optical fiber and artery can obscure light penetration into the vessel wall. One proposed solution is the use of saline flushes. Saline use is limited in duration, however, since myocardial ischemia eventually occurs in the distal myocardium. The inventors have proposed the use of artificial blood substitutes in the place of saline. Artificial hemoglobin or artificial blood including hemoglobin is non-particulate and therefore does not scatter light. Moreover, artificial hemoglobin is about to be approved by the United States Food and Drug Administration as a blood substitute and can carry oxygen necessary to prevent myocardial ischemia. Recently, the inventors demonstrated the viability of using artificial hemoglobin to reduce light scattering by blood in mouse myocardium coronary arteries (Villard J W, Feldman M D, Kim Jeehyun, Milner T O, and Freeman G L. Use of a blood substitute to determine instantaneous murine right ventricular thickening with optical coherence tomography. *Circulation* 2002, Volume 105: Pages 1843-1849, incorporated by reference herein).

An OCT catheter to image coronary plaques has been built and is currently being tested by investigators. (Jang I K, Bouma B E, Hang O H, et al. Visualization of coronary atherosclerotic plaques in patients using optical coherence tomography: comparison with intravascular ultrasound. *JACC* 2002; 3 9: 604-609, incorporated by reference herein). The prototype catheter consists of a single light source and is able to image over a 360 degree arc of a coronary arterial lumen by rotating a shaft that spins the optical fiber. Because the rotating shaft is housed outside of the body, the spinning rod in the catheter must rotate with uniform angular velocity so that the light can be focused for equal intervals of time on each angular segment of the coronary artery. Mechanical drag in the rotating shaft can produce significant distortion and artifacts in recorded OCT images of the coronary artery. Unfortunately, because the catheter will always be forced to make several bends between the entry point in the femoral artery to the coronary artery (e.g., the 180 degree turn around the aortic arch), uneven mechanical drag will result in OCT image artifacts As the application of OCT is shifted from imaging gross anatomical structures of the coronary artery to its capability to image at the level of a single cell, non-uniform rotation of the single fiber OCT prototype will become an increasingly problematic source of distortion and image artifact.

Essentially, current endoscope type single channel OCT systems suffer by non-constant rotating speed that forms irregular images of a vessel target. See U.S. Pat. No. 6,134,003, incorporated by reference herein. The approach of a rotary shaft to spin a single mode fiber is prone to produce artifacts. The catheter will always be forced to make several bends from its entry in the femoral artery, to the 180 degree turn around the aortic arch, to its final destination in the coronary artery. All these bends will cause uneven friction on the rotary shaft, and uneven time distribution of the light on the entire 360 degree arch of the coronary artery. As the application of OCT is shifted from gross anatomical structures of the coronary artery to its capability to image at higher resolutions (i.e., the level of a single cell), then non-uniform rotation of the single fiber OCT will become a greater source of artifact.

The present invention overcomes this disadvantage of current single mode endoscope OCT by putting a rotating part at the end of the fiber probe. The rotating part is driven by biocompatible gas or liquid pumped externally. The rotating part is based on a miniature turbine, screw or water wheel, or nanotechnology. The single mode fiber itself remains stationary, but only a prism reflecting incident light to the target vessel wall will rotate at constant speed.

The present invention pertains to a catheter imaging probe for a patient. The probe comprises a conduit through which energy is transmitted. The probe comprises a first portion through which the conduit extends. The probe comprises a second portion which rotates relative to the conduit to redirect the energy from the conduit.

The present invention also pertains to a rotating tip assembly suitable for use with the inventive catheter imaging probe. The rotating tip assembly comprises generally an axle having a plurality of turbine-like members projecting generally radially outward from a central longitudinal axis of the axle, the axle further having a central longitudinal bore extending along the entire longitudinal axis of the axle. A distal end of the axle is beveled at an angle suitable to permit the reflection or refraction of optical energy at a predetermined angle away from the central longitudinal axis of the axle, then to gather light reflected back from the environment surrounding the catheter tip and transmit the same to the optical fiber. An outer housing having optically transparent properties is provided and is mounted on a distal end of a catheter body. A catheter end cap having a central longitudinal bore and a plurality of fluid flow ports passing through the catheter end cap and oriented co-axial with the longitudinal axis of the catheter end cap and the catheter body is provided. The catheter end cap is affixed within a distal end of the central longitudinal bore in the catheter body, and axle having the plurality of turbine-like members is concentrically and co-axially engaged within the central longitudinal bore of the catheter end cap and is rotatable therein. A second cap is provided which comprises generally concentrically aligned annular members, a first inner annular member defining a central longitudinal bore of the second cap and being in concentric spaced-apart relationship with a second outer cylindrical member so as to define an annular opening there between. The annular opening is maintained by spacer or rib members. The second outer cylindrical member has a plurality of fluid flow ports passing through a distal end surface thereof.

DETAILED DESCRIPTION OF THE PREFERRED EMBODIMENTS

Figure 1:
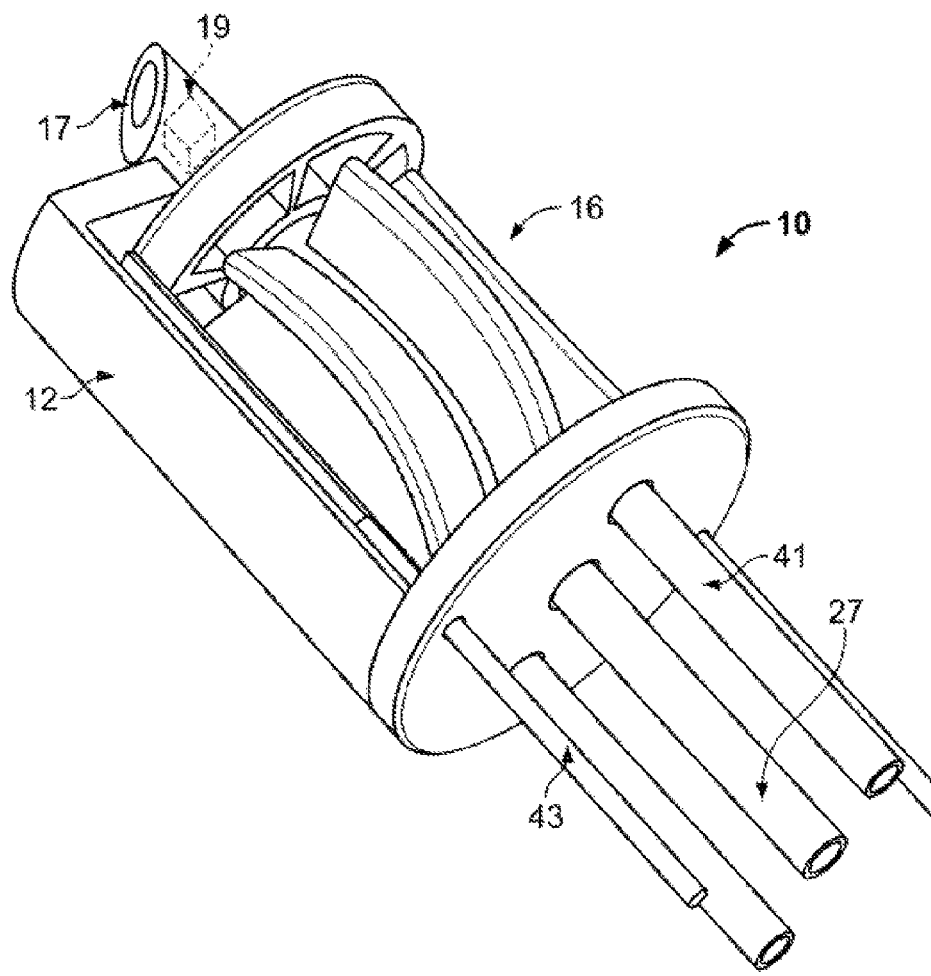
FIG. 1 is a perspective view of the rotating tip assembly of the present invention depicting fluid flows there through and optical inputs.

In the accompanying figures, like elements are identified by like reference numerals among the several preferred embodiments of the present invention. A rotating catheter tip assembly 10 comprises a housing 12 and a turbine 16, as shown in FIG. 1. The housing 12 includes a conduit 27 that extends through the housing 12 and turbine 16, whereby the turbine 16 rotates relative to the conduit 27 to redirect energy from the conduit 27. Preferably, conduit 27 is a radiation waveguide, and more preferably the radiation waveguide is an optical fiber. The rotating catheter tip assembly 10 rotates a reflecting material 17, which then reflects energy emanating from the conduit 27. The reflecting material 17 is coupled with a focusing element 19 to focus the energy from conduit 27 to a target. For purposes of this detailed description, it will be understood that light is redirected from an optical fiber and reflected light from a given in vivo target is then gathered and redirected back to the optical fiber through the focusing element 19. The focusing element 19 may be any type of lens, GRIN lens, and the like suitable to focus optical energy. The focusing element 19 can be attached to the conduit, as to not rotate and alternatively, there is a space in between the focusing element 19 and the conduit 27, whereby the focusing element 19 is attached to turbine 16 as to rotate thereby.

Figure 2:
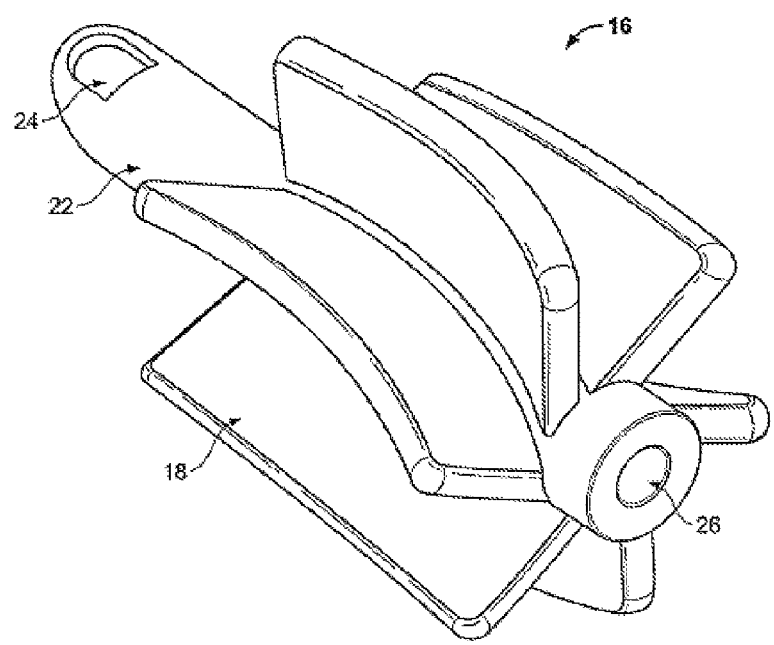
FIG. 2 is a perspective view of a first embodiment of a turbine member in accordance with the present invention.

The turbine 16 includes a center axle 22 and a plurality of vane members 18, as shown in FIG. 2. The center axle 22 includes a central longitudinal bore 26, through which the conduit 27 extends. The center axle 22 includes a window opening 24 at the distal end, through which reflecting material 17 reflects energy emanating from the conduit 27. The vane members 18 project radially outward from center axle 22 and provide a rotating torque to the center axle 22 when a flowing fluid (gas or liquid) flows against the vane members 16, thereby causing the center axle 22 to rotate about the conduit 27. Preferably, the vane members 16 can have a pre-determined curvature along the longitudinal axis of the turbine 16. The vane members 16 can be spiral shaped, or in any other configuration which permits rotation of the turbine 16. Preferably, the turbine 16 is made from stainless steel, plastic tygon or Teflon. Alternatively, the turbine 16 includes knobs to support the axle 22 and allows the axle 22 to rotate without wobbling.

Figure 3:
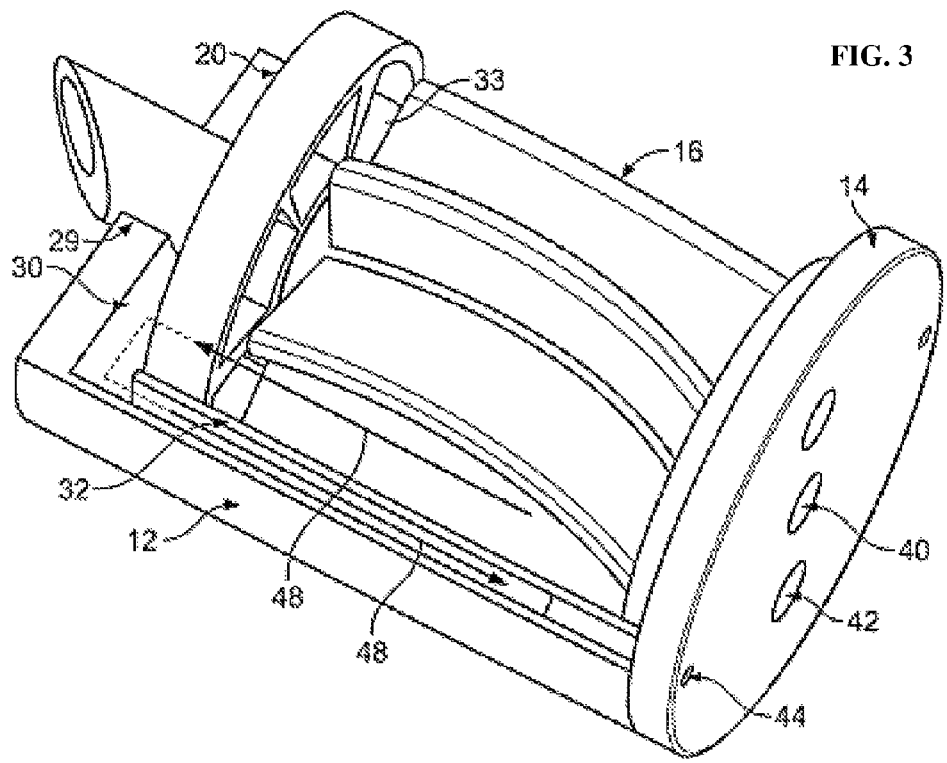
FIG. 3 is a perspective cut-away view of the rotating tip assembly of the present invention.
Figure 4A:
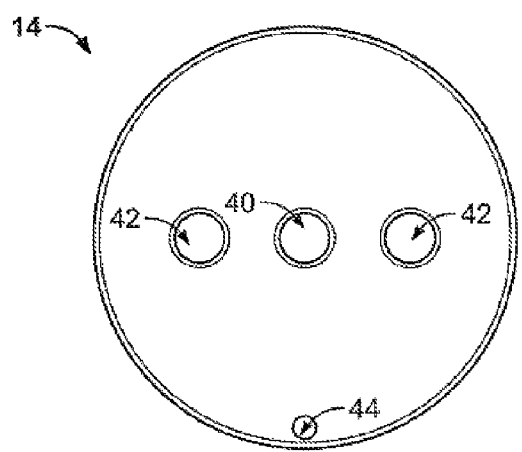
FIG. 4A is an end elevational view of a housing cap for the rotating tip assembly of the present invention.
Figure 4B:
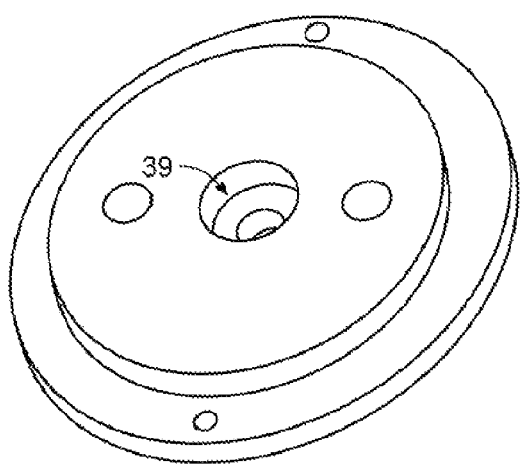
FIG. 4B is a perspective end view of the housing cap for the rotating tip assembly of the present invention.

The housing 12 includes a cylinder 32, a housing cap 14, and a cap member 20, as shown in FIG. 3. The cylinder 32 includes a central chamber 33, a distal opening 29, and outlet channels 30. The central chamber 33 houses the turbine member 16 and includes an inflow and an outflow, which define a fluid flow pathway 48. The inflow runs along the turbine member 16, while the outflow runs along the outlet channels 30. The housing cap 14 includes a plurality of fluid inlet ports 42, a plurality of fluid outlet ports 44, and a central opening 40, as shown in FIGS. 4a and 4b. The fluid inlet ports 42 attach to fluid inlet tubes 41, as shown in FIG. 1. The fluid inlet tubes 41 are connected to a fluid source (not shown). The fluid inlet ports 42 pass through a generally central portion of the housing cap 14, to transmit fluid to central chamber 33. The fluid inlet ports 42 generally align with turbine member 16. The fluid outlet ports 44 pass through a relatively peripheral portion of the housing 14 and align with the outlet channels 30 and outlet tubes 43, as shown in FIG. 1. The central opening 40 includes a concentric recessed seat 39, as shown in FIG. 4, in which the axle 22 sits and substantially rotates thereabout. Concentric recessed seat 39 is formed to permit the axle 22 to rotate without wobbling. The central opening 40 co-axially aligns with longitudinal bore 26 and permits conduit 27 to be passed there through, whereby the turbine member 16 is freely rotatable without rotate conduit 27. The axle 22 is co-axially aligned to an opening 29 at a distal end of the housing 12 and opening 29 permits axle to rotate about an axis. Preferably the housing 12 is made from Teflon. Alternatively, the housing 12 includes a cover transparent to the energy and which encapsulates the turbine 16, so that no fluid can escape from the housing except through the channels 30. Preferably, the transparent cover is made from any biocompatible transparent plastic. Such plastic can include Polymethyl methacrylate (PMMA) or the like.

Figure 5A:
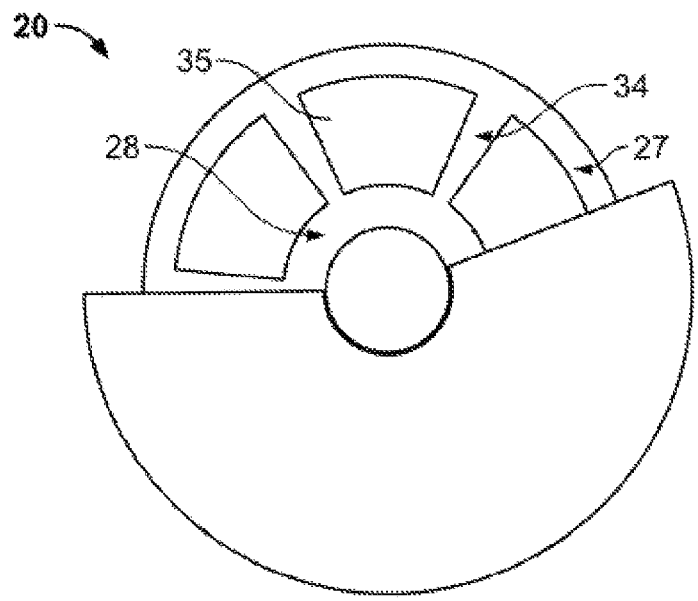
FIG. 5A is a side end elevational view of the cap member for the rotating tip assembly of the present invention.
Figure 5B:
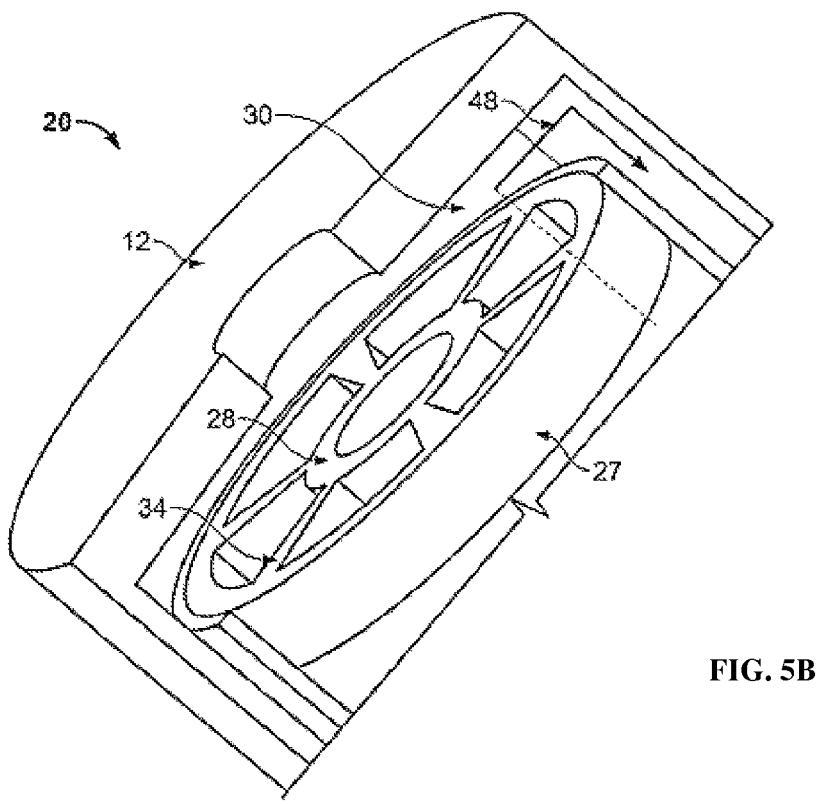
FIG. 5B is a perspective view of the cap member for the rotating tip assembly of the present invention

The cap member 20 includes an inner annular member 28, an outer annular member 27, a plurality of spacer rib members 34, and a plurality of spaces 35, as shown in FIGS. 5a and 5b. The cap member 20 is concentrically mounted onto the distal end of the axle 22 through inner annular member 28, as shown in FIG. 5b. The inner annular member 28 permits axle 22 to freely rotate thereabout, without wobbling. The inner annular member 28 and outer annular member 27 are connected by spacer rib members 34 and are concentrically spaced apart. The spaces 35 between adjacent pairs of spacer rib members 34 provide outflow pathways for the fluid flow 48 to pass from the central chamber 33 to the distal end of housing 12 and then to outlet channels 30. A plurality of fluid flow ports (not shown) may be provided in a distal surface of the cap member 20 and define a distal end of spaces 35 to channel fluid flow out of spaces 35.

At the distal end of the axle 22, a reflecting material 17 (not shown) is attached to the center axle 22 at window 24, as shown in FIG. 1. The reflecting material redirects energy from the conduit 27. The reflecting material preferably includes a prism or a minor, which reflects energy from the conduit, the prism rotating with the center axle 22. In one embodiment the energy is radiant energy. Preferably, a lens focuses energy onto the patient. The lens can be a microlens, GRIN lens, or optical fiber lines. The probe preferably includes a fluid source connected to the inlet tube.

The fluid is provided to the inlet tubes 41, as shown in FIG. 1. The fluid is provided by a fluid source (not shown). Preferably, the fluid source is a pump. The pump can be any standard fluid pump, as known and recognized by those skilled in the art. Preferably, the fluid is chosen from a group consisting of oxygen, carbon dioxide, nitrogen, helium, saline, water, d5W or artificial blood such as Oxyglobin. Alternatively, any gas that can be dissolved into blood or tissue relatively easily can be used. Accordingly, a gas pump would used to provide fluid to the inlet tubes 41.

The preferred dimensions of the outer diameter of the housing 12 is 2 mm, the outer diameter of the turbine 16 is 1.4 mm, the outer diameter of the inlet tube 42 is 0.2 mm, the outer diameter of the outlet tube 44 is 0.2 mm. The speed can be 30 rotations per second. The turbine pitch can be 4 pitch/mm, while the speed of the gas flow can be 120 mm/sec and target flow rate is 3 mm$^3$/sec. The above are all examples. The invention is not limited to these values. For instance, to obtain a finer image, the flow rate is lower and the time it takes to obtain an image is then longer.

Alternatively, the turbine 16 includes wart to reflect energy coming through a radiation energy guide back to the radiation energy guide. The reflective wart can be any reflective material on the axle 22. Preferably, the wart is block shape with a flat wall shape. The wart rotates with the turbine and the energy reflected by the wart indicates current angular position of the prism. The wart identifies one angular position of the rotating portion when the light hits and gets back form the wart. The wart may be a flat wall facing the radiation energy guide to reflect back. The wart can be molded into the axle, and flat wall can have a reflective material, such as a minor placed on it to increase the reflection. The width of the wart is small compared to the circumference of axle 22, so as to identify a given point, and is high enough to block the energy emitted from optical fiber, so it is reflected by wart.

In operation, the assembly may be connected to a sample arm of a single mode fiber OCT. In the center of an OCT probe, the turbine 16 is connected to a prism. Gas or liquid flows through the inlet port 42 into the turbine chamber 32. The turbine 16 is supported by positioning between the housing cap 14 and cap member 20 to maintain constant position during rotation. At the center of the turbine 16, the central longitudinal bore 26 includes an optical fiber. During rotation of the turbine 16, the optical fiber remains stationary. In spectral domain phase sensitive OCT, the reference reflecting surface is within the catheter.

A probing light will be launched from the single mode optical fiber through a lens having a curvature to focus the light onto target tissue area. A rotating prism connected to the turbine reflects incoming light toward target tissue area on the vessel wall, enabling the imaging system to scan 360 degrees around an inner vessel wall at a constant speed. The reflected light from the target tissue returns to the fiber through the prism. A standard analysis of the light is then performed to obtain the image, as in U.S. Pat. No. 6,134,003, incorporated by reference herein. Gas or liquid gone through the turbine 16 exits the probe through an outlet tube 44. The rotation direction and speed of the turbine are controlled by the pressure difference between inlet ports 42 and outlet ports 44. Applying a gas or liquid through an inlet tube pressure is induced to the turbine which rotates; therefore, a prism put on the end of the turbine rotates as well. Finally, an imaging system can scan 360 degrees around the inner vessel wall at a constant speed.

Figure 6:
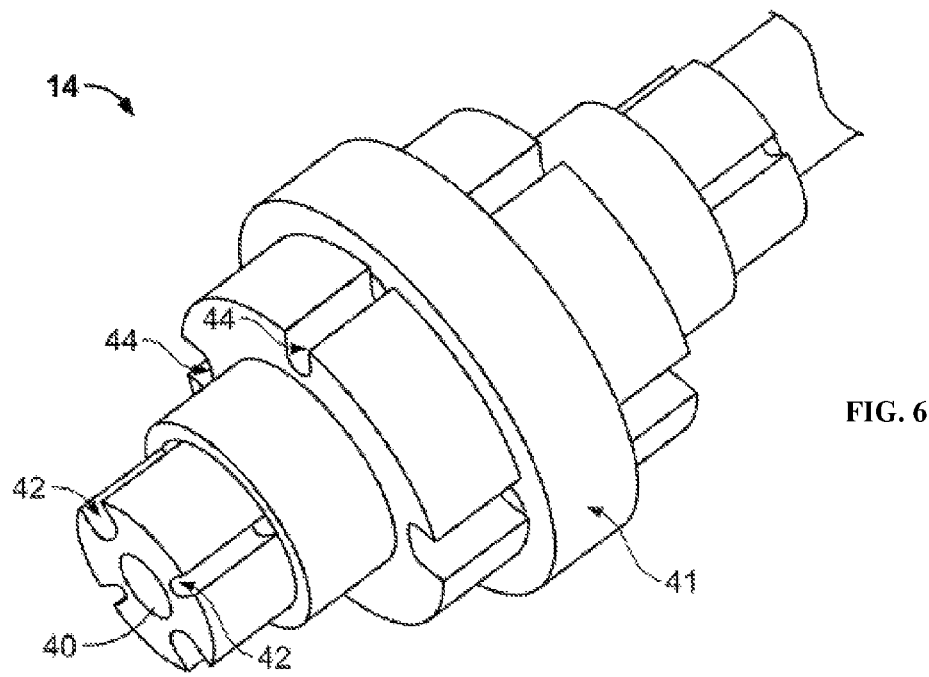
FIG. 6 is an end elevational view of an alternative embodiment of the housing cap in accordance with the present invention.
Figure 7:
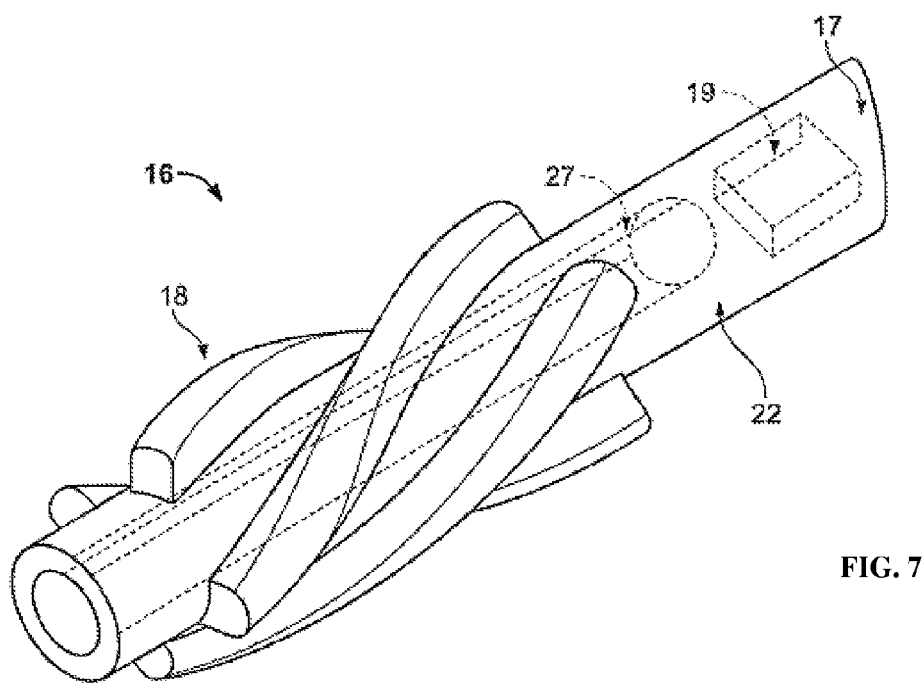
FIG. 7 is a perspective view of an alternative embodiment of the turbine member in accordance with the present invention.

FIG. 6 depicts an alternative embodiment of a housing cap 14, synonymously termed a catheter cap 14, which is mountable on a distal open end of a catheter body (not shown) such that central flange 41 seats against the distal end of the catheter body (not shown). The fluid inlet openings 42 and fluid outlet openings 44 consist of channels which permit fluid flow to pass through the catheter cap 14 in the manner discussed above. Central opening 40 again accommodates passage of the optical fiber 27 therethrough and is co-axially aligned with the central bore of 26 of the turbine member 16 as depicted in FIG. 7. The proximal and distal ends of the catheter cap 14 projects from the central flange 41 and are preferably minor images of one another about the central flange 41.

An alternative embodiment of the turbine member 16 is illustrated in FIG. 7. The principal difference between the first embodiment of the turbine member illustrated in FIGS. 1-5 is that there is a space in between the focusing element 19 and the conduit 27. The space may be an air space or an optical gap providing for the optical energy permission to expand before being focused by the focusing element. In this embodiment, the focusing element 19 and the reflecting material 17 both rotate about the axis by the axle 22, by being substantially connected to the axle by optical glue, or the like. Also, the curved or helical pitch of the turbine vanes 18 is greater than that depicted in FIGS. 1-5, such that they subtend approximately a 90 degree arc about the circumference of the axle 22.

Figure 8:
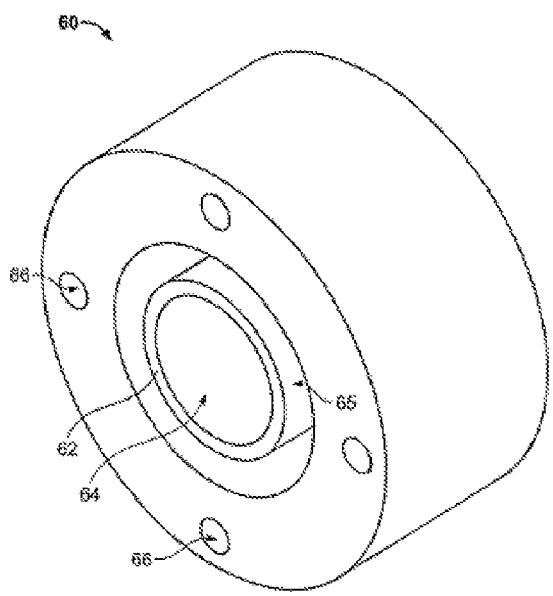
FIG. 8 is a perspective view of an alternative embodiment of the second cap member in accordance with an embodiment of the present invention.

A second embodiment of a cap member 20 is depicted in FIG. 8, and is synonymously termed second cap member 60. The second cap member 60 includes a central opening 64, a collection channel 65 and a plurality of outflow ports 66. The central opening 64 is concentrically mounted onto the distal end of the axle 22 to permit axle 22 to rotate freely thereabout. The collection channel 65 is connected to the outflow ports 66, to permit the outflow of fluid. The outflow ports are substantially aligned with the outflow ports 66 of the catheter cap 14, to allow the outflow to return to the fluid source (not shown). Second cap member 60 is similar to second cap member 60, in that it has an inner annular member 64 through which the axle 22 of turbine member, and an outer annular member 62 which is in concentrically spaced apart relationship therewith 16 passes except that after fluid flows through the spaces 35 it enters a return path by passing through outlet flow ports 66 which are provided about a peripheral portion of a distal surface of the second cap member 60 and enter the fluid outlet channels 30 in the housing 12.

Figure 9:
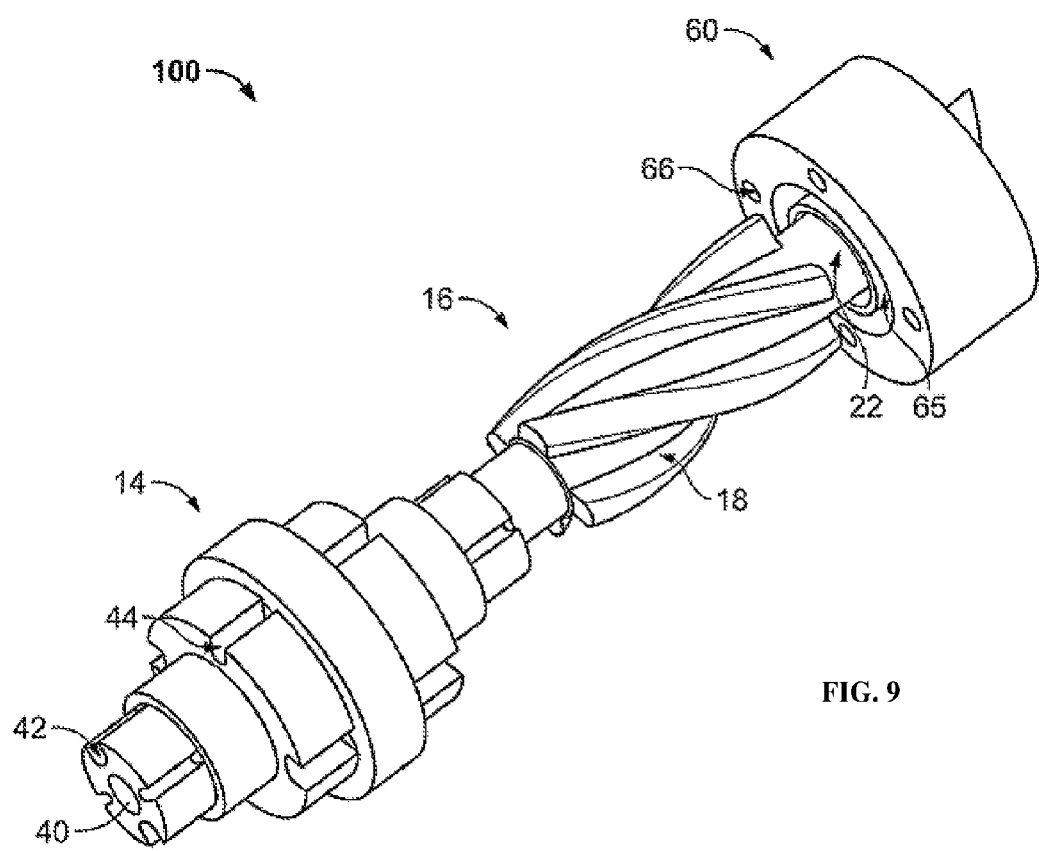
FIG. 9 is a perspective view of an alternative embodiment of the rotating tip assembly in accordance with the present invention.

FIG. 9 demonstrates the complete assembly 100 of the catheter cap 14, second cap member 60, with turbine member 16 therebetween.

The present invention also pertains to a method for imaging a patient. The method comprises the steps of inserting a catheter into a patient, rotating a turbine 16 of the catheter relative to a conduit 27, extending through the turbine 16 of the catheter, redirecting energy transmitted through the conduit 27 to the patient and receiving the energy reflected or backscattered to the turbine, and redirecting reflected energy to the conduit 27.

Preferably, the rotating step includes flowing fluid through an inlet tube 41 to the turbine 16 to turn an axle 22 of the turbine 16.

Preferably, the flowing step includes flowing the fluid against a plurality of vane members 18 which extend from a rotating center axle 22 of the turbine 16 to create a rotating torque on the center axle 22 to rotate about the conduit 27 that extends through the center axle 22. The axle 22 preferably has reflecting material 17 attached to the distal end of the axle 22, which redirects the energy from the conduit 27. Preferably, the conduit 27 is an optical fiber.

The reflecting material 17 preferably includes a prism or minor which reflects light from the conduit, and includes rotating the prism with the axle as the axle is rotated by the flowing fluid. Preferably, the rotating step includes the step of rotating the center axle 22 that is supported by knobs of the cylinder of the turbine in which the center axle 22 is disposed. Preferably, flowing the fluid from the inlet tube 41 through a chamber 33 and removing the fluid flowing from the housing 12 through at least one outlet tube 43.

In the foregoing described embodiment of the invention, those of ordinary skill in the art will understand and appreciate that an assembly is described which provides a fluid drive mechanism for rotating a minor about the central longitudinal axis of the assembly while transmitting optical energy from a co-axial optical fiber which is maintained stationary within the central axis of the assembly, such that light energy may be reflected or refracted perpendicular to the central longitudinal axis of the catheter and traverse a 360 degree arc.

What is claimed:

1. A rotating catheter aassembly, comprising:
   a housing;
   a turbine, the turbine disposed within the housing,
   wherein the housing includes a central opening that coaxially aligns with a longitudinal bore through the turbine;

a conduit that extends through the central opening and the longitudinal bore of the housing and the turbine, respectively; and a reflecting material disposed at one end of the turbine, a fluid drive system operably coupled within the housing and the turbine, wherein the housing, the turbine, the conduit, the reflecting material, and the fluid drive system form a rotating catheter assembly;

whereby the turbine rotates around the conduit by the fluid drive system, such that an optical energy emitted from the conduit and reflected by the reflecting material is redirected by the rotation of the turbine.

2. A rotating catheter tip assembly, comprising:

a housing and a turbine; wherein the housing includes a conduit that extends through the housing and the turbine, whereby the turbine rotates relative to the conduit to redirect an energy from the conduit, wherein a reflecting material that reflects energy emanating from the conduit and the reflecting material coupled with a focusing element to focus the energy from conduit to a target;

the turbine includes a center axle and a plurality of vane members, wherein the center axle includes a window opening at the distal end, through which the reflecting material reflects the energy emanating from the conduit;

the vane members project radially outward from the center axle and provide a rotating torque to the center axle when a flowing fluid flows against the vane members, thereby causing the center axle to rotate about the conduit;

the housing includes a cylinder, a housing cap, and a cap member, wherein the cylinder includes a central chamber, a distal opening, and a plurality of outlet channels;

the central chamber houses the turbine and includes an inflow and an outflow that define a fluid flow pathway for the flowing fluid, wherein the inflow runs along the turbine while the outflow runs along the outlet channels;

the housing cap includes a plurality of fluid inlet ports, a plurality of fluid outlet ports, and a central opening, wherein the fluid inlet ports attach to a plurality of fluid inlet tubes and the fluid inlet tubes are connected to a fluid source.

3. The rotating catheter tip assembly of claim 2, wherein the fluid inlet ports pass through a central portion of the housing cap, to transmit fluid to the central chamber and the fluid inlet ports align with the turbine; and the fluid outlet ports pass through a relatively peripheral portion of the housing and align with a plurality of outlet channels and a plurality outlet tubes.

4. The rotating catheter tip assembly of claim 3, wherein the central opening includes a concentric recessed seat in which the center axle sits and substantially rotates thereabout without wobbling; the central opening co-axially aligns with longitudinal bore and permits the conduit to be passed there through, whereby the turbine is freely rotatable without rotating the conduit; the axle is co-axially aligned to an opening at a distal end of the housing and the central opening permits axle to rotate about an axis.

5. The rotating catheter tip assembly of claim 2, wherein the cap member includes an inner annular member, an outer annular member, a plurality of spacer rib members, and a plurality of spaces, wherein the cap member is concentrically mounted onto the distal end of the axle through the inner annular member; the inner annular member permits the axle to freely rotate thereabout, without wobbling; and the inner annular member and the outer annular member are connected by the spacer rib members and are concentrically spaced apart, wherein the spaces between adjacent pairs of spacer rib members provide the outflow pathways for the fluid flow to pass from the central chamber to the distal end of housing and then to the outlet channels.

6. The rotating catheter tip assembly of claim 5, wherein the focusing element is attached to the conduit as to not rotate.

7. The rotating catheter tip assembly of claim 6, further comprising a space in between the focusing element and the conduit, whereby the focusing element is attached to turbine as to rotate thereby.

8. The rotating catheter tip assembly of claim 7, wherein the vane members have a pre-determined curvature along the longitudinal axis of the turbine.

9. The rotating catheter tip assembly of claim 8, further comprising a plurality of fluid flow ports provided in a distal surface of the cap member and to define a distal end of spaces to channel the fluid flow out of the spaces.

10. The rotating tip assembly as described in claim 8, further comprising a cover having at least a portion which is transparent to the energy which encapsulates the housing and contacts the turbine so no fluid can escape from the housing except through at least one outlet tube.

11. The rotating tip assembly as described in claim 10, further comprising a plurality of fluid flow ports provided in a distal surface of the cap member and to define a distal end of spaces to channel the fluid flow out of the spaces.

12. The rotating tip assembly as described in claim 10, wherein the transparent cover is made from any biocompatible transparent plastic.

13. The rotating tip assembly as described in claim 12, wherein the focusing element is selected from the group consisting of a lens, mirror, lens/mirror combination, prism and liquid crystal.

14. The rotating tip assembly as described in claim 13, wherein the axle includes a wart to redirect energy back to the optical fiber to indicate angular position.

15. The rotating tip assembly as described in claim 14, where the fluid source includes a pump which pumps the fluid from the fluid source.

16. The rotating tip assembly as described in claim 15, wherein the center axle includes a plurality of turbine-like members projecting radially outward from a central longitudinal axis of the axle.

17. A method for operating a catheter, the catheter comprising a conduit through which optical energy is transmitted; and a first portion through which the conduit extends, the first portion including an inlet tube through which fluid flows; a second portion which provides rotational movement relative to the conduit to redirect the optical energy from the conduit, wherein the second portion comprises a rotating catheter tip assembly, wherein the method comprising the steps of:

rotating a second portion of a catheter relative to the conduit extending through a first portion of the catheter by flowing a fluid against the vane members which extend from a rotating center axle of a turbine of the second portion to create a rotating torque on the center axle that causes center axle to rotate about the conduit that extends through the center axle;

redirecting an optical energy transmitted through the conduit to a target from the second portion;

receiving the energy reflected back to the second portion from a target; and redirecting the reflected energy to the conduit.

18. The method as described in claim 17, wherein the rotating step includes the step of flowing a fluid through an inlet tube to the second portion to rotate the second portion.

19. The method as described in claim 18 comprising flowing the fluid against vane members which extend from a rotating center axle of a turbine of the second portion to create a rotating torque on the center axle that causes center axle to rotate about the conduit that extends through the center axle.

20. The method as described in claim 19, wherein the conduit does not rotate when the second portion of the catheter rotates.

* * * * *